United States Patent [19]
Greene et al.

[11] Patent Number: 5,786,193
[45] Date of Patent: Jul. 28, 1998

[54] HUMAN GERANYLGERANYL PYROPHOSPHATE SYNTHETHASE

[75] Inventors: John M. Greene, Gaithersburg; Ewen F. Kirkness, Olney; Craig A. Rosen, Laytonsville, all of Md.

[73] Assignee: Human Genome Sciences, Inc., Rockville, Md.

[21] Appl. No.: 469,665

[22] Filed: Jun. 6, 1995

[51] Int. Cl.$^6$ .............................. C12N 9/10; C12N 15/54; C12N 15/63; C12N 15/79
[52] U.S. Cl. ..................... 435/193; 435/69.1; 435/252.3; 435/320.1; 536/23.2; 536/24.31
[58] Field of Search ................................ 435/183, 252.3, 435/320.1, 69.1, 193; 536/23.2, 24.31

[56] References Cited

U.S. PATENT DOCUMENTS

| | | | |
|---|---|---|---|
| 5,304,478 | 4/1994 | Bird et al. | 435/172.3 |
| 5,420,245 | 5/1995 | Brown et al. | 530/328 |
| 5,429,939 | 7/1995 | Misawa et al. | 435/67 |
| 5,443,978 | 8/1995 | Ellenberger et al. | 435/193 |
| 5,530,188 | 6/1996 | Ausich et al. | 800/205 |
| 5,530,189 | 6/1996 | Ausich et al. | 800/205 |

OTHER PUBLICATIONS

Sheares, B. T., et al., Biochemistry, vol. 28, "Cloning, analysis, and bacterial expression of human farnesyl pyrophosphate synthetase and its regulation in Hep G2 cells", pp. 8129–8135, 1989.

Wilkin, D. J., et al., The Journal of Biological Chemistry, vol. 265, "Isolation and sequence of the human farnesyl pyrophosphate synthetase c DNA", pp. 4607–4614, 1990.

Kuntz, M., et al., The Plant Journal, vol. 2, "Identification of a cDNA for the plastid–located geranylgeranyl pyrophosphate synthase from *Capsium annuum*: correlative increase in enzyme activity and transcript level during fruit ripening", pp. 25–34, 1992.

EMBL nucleotide sequence database Accession No. Z44596, Locus HSC25A041, "*H. sapiens* partial cDNA sequence; clone c–25a04.", 1994.

GenBank nucleotide sequence database Accession No. R61164, Locus R61164, "yh10f02.r1 *Homo sapiens* cDNA clone 42865 5'", 1995.

GenBank/EST nucleotide sequence database Accession No. T31667, "EST36765 *Homo sapiens* cDNA 5'end similar to None.", 1995.

Primary Examiner—Robert A. Wax
Assistant Examiner—William W. Moore
Attorney, Agent, or Firm—Elliot M. Olstein; J. G. Mullins

[57] ABSTRACT

A human geranylgeranyl pyrophosphate synthetase polypeptide and DNA (RNA) encoding such polypeptide and procedure for producing such polypeptide by recombinant techniques is disclosed. Also disclosed are methods for utilizing such polypeptide for controlling morphology of cells. Antagonist against such polypeptides and their use as a therapeutic to treat cancer is also disclosed. Diagnostic assays are also disclosed which detect the presence of a mutated form of hGGPS and over-expression of the hGGPS protein.

18 Claims, 7 Drawing Sheets

```
                         1                                                              50
ggps2.msf(Neurospora)    MAVTSSSPGP  APLSLLSNND  DFIAPFNINT  KFPSAIVPPR  TSSNQPISVA
ggps2.msf(Human_GGPS)    ..........  ..........  ..........  ..........  ..........
            Consensus    ----------  ----------  ----------  ----------  ----------

51                                                             100
ggps2.msf(Neurospora)    IPSNRISSAG  LAATQQAQTR  KRKASVAQIS  LPSKLPTSFS  PYTMAFQPFQ
ggps2.msf(Human_GGPS)    ..........  ..........  ..........  ..........  ..........
            Consensus    ----------  ----------  ----------  ----------  ----------

101                                                            150
ggps2.msf(Neurospora)    PPPNPDRFAT  EDFFSPSRRT  WSEEKEKVLT  GPYDYLNGHP  GKDIRSQMVK
ggps2.msf(Human_GGPS)    ..........  .......MEK  TQETVQRILL  EPYKYLLQLP  GKQVRTKLSQ
            Consensus    ----------  ----------  --E-----L-  -PY--YL---P  GK--R-----

151                                                            200
ggps2.msf(Neurospora)    AFDAWLDVPS  ESLEVITKVI  SMLHTASLLV  DDVEDNSVLR  RGFPVAHSIF
ggps2.msf(Human_GGPS)    AFNHWLKVPE  DKLQIIIEVT  EMLHNASLLI  DDIEDNSKLR  RGFPVAHSIY
            Consensus    AF--WL-VP-  --L--I--V-  -MLH-ASLL-  DD-EDNS-LR  RGFPVAHSI- 201                                                            250
ggps2.msf(Neurospora)    GIPQTINTSN  YVYFYALQEL  QKLKNPKAVS  IFSEELLNLH  RGQGMDLFWR
ggps2.msf(Human_GGPS)    GIPSVINSAN  YVYFLGLEKV  LTLDHPDAVK  LFTRQLLELH  QGQGLDIYWR
            Consensus    GIP--IN--N  YVYF--L---  --L--P-AV-  -F---LL-LH  -GQG-D--WR 251                                                            300
ggps2.msf(Neurospora)    DTLTCPTEDD  YLEMVSNKTG  GLFRLGIKLM  QAESRSPVDC  VPLVNIIGLI
ggps2.msf(Human_GGPS)    DNYTCPTEEE  YKAMVLQKTG  GLFGLAVGLM  QLFSDYKEDL  KPLLNTLGLF
            Consensus    D--TCPTE--  Y--MV--KTG  GLF-L---LM  Q--S----D-  -PL-N--GL- 301                                                            350
ggps2.msf(Neurospora)    FQIADDYHNL  WNREYTANKG  MCEDLTEGKF  SFPVIHSIRS  NPSNMQLLNI
ggps2.msf(Human_GGPS)    FQIRDDYANL  HSKEYSENKS  FCEDLTEGKF  SFPTIHAIWS  RPESTQVQNI
            Consensus    FQI-DDY-NL  ---EY--NK-  -CEDLTEGKF  SFP-IH-I-S  -P---Q--NI 351                                                            400
ggps2.msf(Neurospora)    LKQKTGDEEV  KRYAVAYMES  TGSFEYTRKV  IKVLVDRARQ  MTEDIDDGRS
ggps2.msf(Human_GGPS)    LRQRTENIDI  KKYCVHYLED  VGSFEYTRNT  LKELEAKAYK  QI.DARGGNF
            Consensus    L-Q-T-----  K-Y-V-Y-E-  -GSFEYTR--  -K-L---A--  ---D---G--

401                          428
ggps2.msf(Neurospora)    KSGGIHKILD  RIMLHQEENV  AQKNGKKE
ggps2.msf(Human_GGPS)    ELVALVKHLS  KMFKEENE..  ........
            Consensus    ------K-L-  -------E--  --------
```

FIG. 1A

```
1    ATGGAGAAGACTCAAGAGACAGTCCAAAGAATTCTCTAGA
     M   E   K   T   Q   E   T   V   Q   R   I   L   E
42   ACCTATAAATACTTACTCAGTTACCAGGTAAACAAGTGA
     P   Y   K   Y   L   Q   L   P   G   K   Q   V
83   GAACCAAACTTTCACAGGCATTAATCATTGGCTGAAAGTT
     R   T   K   L   S   Q   A   F   N   H   W   L   K   V
124  CCAGAGGACAAGTTACTACAGATTATTATTGAAGTGACAGAAAT
     P   E   D   K   L   Q   I   I   I   E   V   T   E   M
165  GTTGCATAATGCCAGTTACTTACTCATCGATGATATTGAAGACA
     L   H   N   A   S   L   L   I   D   D   I   E   D
206  ACTCAAAACTCCGAGGCTTCCAGTGCCCACAGCATC
     N   S   K   L   R   R   G   F   P   V   A   H   S   I
```

FIG. 1B

```
247  TATGGAATCCATCTGTCATCAATTCCAATTAGTGTA
      Y  G  I  P  S  V  I  N  S  N  Y  V  V
288  TTTCCTTGGCTTGAGAAAGTTAACCTTGATCACCCAG
      F  L  G  L  E  K  V  L  T  L  D  H  P
329  ATGCAGTTGAAGCTTTTACCCGCCAGCTTTTGGAACTCCAT
      D  A  V  K  L  F  T  R  Q  L  L  E  L  H
370  CAGGGACAAGGCCTAGATATTTACTGGAGGGATAATTACAC
      Q  G  Q  G  L  D  I  Y  W  R  D  N  Y  T
411  TTGTCCCACTGAAGAAGAATATAAAGCTATGGTGCTGAGA
      C  P  T  E  E  E  Y  K  A  M  V  L  Q
452  AAACAGGTGGACTTGATTAGCAGTAGGTCTATGCAG
      K  T  G  G  L  F  G  L  A  V  G  L  M  Q
```

FIG. 1C

```
493  TTGTTCTCTGATTACAAAGAAGATTTAAAACCGTTACTTAA
      L  F  S  D  Y  K  E  D  L  K  P  L  L  N

534  TACACTTGGGCTCTTTTCCAATTAGGATGATTATGCTA
      T  L  G  L  F  F  Q  I  R  D  D  Y  A

575  ATCTACACTCCAAAGAATATAGTAAACAAAGTTTGGT
      N  L  H  S  K  E  Y  S  E  N  K  S  L  G

616  GAAGATTCTGACAGAGGAAGTTCATTCCTACTATTCA
      E  D  L  T  E  G  K  F  S  F  P  T  I  H

657  TGCTATTTGGTCAAGTCTGAAAGCACCAGGTCAGAATA
      A  I  W  S  R  S  E  S  T  Q  V  Q  N
```

FIG. 1D

```
698  TCTTGGCCAGAGAACAGAAACATAGATATAAAAAATAC
      I  L  R  Q  R  T  E  N  I  D  I  K  K  Y
739  TGTGTACATTATCTTGAGGATGTAGGTTCTGGGAATACAC
      C  V  H  Y  L  E  D  V  G  S  G  E  Y  T
780  TCGTAATACCCTTAAGAGCTTGAAGCTAAAGCTATAAAC
      R  N  T  L  K  E  L  E  A  K  A  Y  K
821  AGATTGATGCACGTGGTGGAACCTGAGTAGCCTTA
      Q  I  D  A  R  G  G  N  P  E  L  V  A  L
862  GTAAAACACTTAAGATGTCCAAGAAAATGAATA
      V  K  H  L  S  K  M  S  K  E  E  N  E  .
903  A
```

FIG. 2

```
Query:  16  ETVQRILLEPYKYLLQLPGKQVRTKLSQAFNHWLKVPEDKLQIIEVTEMLHNASLLIDD  195
            E  +++L  PY YL  PGK +R+++ +AF+ WL VP +  L++I +V  MLH ASLL+DD
Sbjct: 123  EEKEKVLTGPYDYLNGHPGKDIRSQMVKAFDAWLDVPSESLEVITKVISMLHTASLLVDD  182

Query: 196  IEDNSKLRRGFPVAHSIYGIPSVINSANYVYFLGLEKVLTLDHPDAVKLFTRQLLELHQG  375
            +EDNS LRRGFPVAHSI+GIP  IN++NYVYF L+++  L +P AV  +F+ +LL LH+G
Sbjct: 183  VEDNSVLRRGFPVAHSIFGIPQTINTSNYVYFYALQELQKLKNPKAVSIFSEELLNLHRG  242

Query: 376  QGLDIYWRDNYTCPTEEYKAMVLQKTGGLFGLAVGLMQLFSDYKEDLKPLLNTLGLFFQ   555
            QG+D++++WRD  TCPTE++Y  MV  KTGGLF L + LMQ S  D  PL+N +GL FQ
Sbjct: 243  QGMDLFWRDTLTCPTEDDYLEMVSNKTGGLFRLGIKLMQAESRSPVDCVPLVNIIGLIFQ   302

Query: 556  IRDDYANLHSKEYSENKSFCEDLTEGKFSFPTIHAIWSRPESTQVQNILRQRTENIDIKK  735
            I DDY NL ++EY+ NK   CEDLTEGKFSFP IH+I S P + Q+ NIL+Q+T + ++K+
Sbjct: 303  IADDYHNLWNREYTANKGMCEDLTEGKFSFPVIHSIRSNPSNMQLLNILKQKTGDEEVKR  362

Query: 736  YCVHYLEDVGSFEYTRNTLKELEAKA  813
            Y V  Y+E  GSFEYTR  +K L  +A
Sbjct: 363  YAVAYMESTGSFEYTRKVIKVLVDRA  388
```

FIG. 3A

```
                       1                                                                         50
ggps2.msf(Neurospora)  MAVTSSSPGP APLSLLSNND DFIAPFNINT KFPSAIVPPR TSSNQPISVA
ggps2.msf(Human_GGPS)  .......... .......... .......... .......... ..........
            Consensus  ---------- ---------- ---------- ---------- ----------

51                                                                       100
ggps2.msf(Neurospora)  IPSNRISSAG LAATQQAQTR KRKASVAQIS LPSMLPTSFS PYTMAPQPPQ
ggps2.msf(Human_GGPS)  .......... .......... .......... .......... ..........
            Consensus  ---------- ---------- ---------- ---------- ----------

101                                                                      150
ggps2.msf(Neurospora)  PPPNPDRFAT EDFFSPSRRT WSEEKEKVLT GPYDYLNGHP GKDIRSQMVK
ggps2.msf(Human_GGPS)  .......... .....MEK TQETVQRILL EPYKYLLQLP GKQVRTKLSQ
            Consensus  ---------- -----  --- -E------L- -PY-YL---P GK--R-----

151                                                                      200
ggps2.msf(Neurospora)  AFDAWLDVPS ESLEVITKVI SMLHTASLLV DDVEDNSVLR RGFPVAHSIF
ggps2.msf(Human_GGPS)  AFNHWLKVPE DKLQIIIEVT EMLHNASLLI DDIEDNSKLR RGFPVAHSIY
            Consensus  AF--WL-VP- --L--I--V- -MLH-ASLL- DD-EDNS-LR RGFPVAHSI- 201                                                                      250
ggps2.msf(Neurospora)  GIPQTINTSN YVYFYALQEL QKLKNPKAVS IFSEELLNLH RGQGMDLFWR
ggps2.msf(Human_GGPS)  GIPSVINSAN YVYFLGLEKV LTLDHPDAVK LFTRQLLELH QGQGLDIYWR
            Consensus  GIP--IN--N YVYF--L--- --L--P-AV- -F----LL-LH -GQG-D--WR
```

FIG. 3B

```
                      251
ggps2.msf(Neurospora) DTLTCPTEDD YLEMVSNKTG GLFRLGIKLM QAESRSPVDC VPLVNIGLI
ggps2.msf(Human_GGPS) DNYTCPTEEE YKAMVLQKTG GLFGLAVGLM QLFSDYKEDL KPLLNTLGLF
            Consensus D--TCPTE--  Y--MV--KTG GLF-L---LM Q--S----D- -PL-N--GL-
                                                                       300

301
ggps2.msf(Neurospora) FQIADDYHNL WNREYTANKG MCEDLTEGKF SFPVIHSIRS NPSNMQLLNI
ggps2.msf(Human_GGPS) FQIRDDYANL HSKEYSENKS FCEDLTEGKF SFPTIHAIWS RPESTQVQNI
            Consensus FQI-DDY-NL ---EY--NK- -CEDLTEGKF SFP-IH-I-S -P---Q--NI
                                                                       350

351
ggps2.msf(Neurospora) LKQKTGDEEV KRYAVAYMES TGSFEYTRKV IKVLVDRARQ MTEDIDDGRG
ggps2.msf(Human_GGPS) LRQRTENIDI KKYCVHYLED VGSFEYTRNT LKELEAKAYK QI.DARGGNP
            Consensus L-Q-T----- K-Y-V-Y-E- -GSFEYTR-- -K-L----A- ---D---G--
                                                                       400

401                     428
ggps2.msf(Neurospora) KSGGIHKILD RIMLHQEENV AQKNGKKE
ggps2.msf(Human_GGPS) ELVALVKHLS KMFKEENE.. ........
            Consensus ------K-L- ------E-- --------
```

HUMAN GERANYLGERANYL PYROPHOSPHATE SYNTHETHASE

This invention relates to newly identified polynucleotides, polypeptides encoded by such polynucleotides, the use of such polynucleotides and polypeptides, as well as the production of such polynucleotides and polypeptides. More particularly, the polypeptide of the present invention is Human Geranylgeranyl Pyrophosphate Synthetase, sometimes hereinafter referred to as "hGGPS". The invention also relates to inhibiting the action of such polypeptides.

The regulation, functional activation and intracellular targeting of biological macromolecules are often mediated through the covalent attachment of specific moieties. The post-translational modification of specific proteins by phosphorylation, glycosylation, acetylation, fatty acylation, and methylation has been studied extensively, and a variety of critical biological functions have been ascribed to these particular side groups. In contrast to these familiar types of chemical modification, protein prenylation is a process which refers to the covalent modification of a molecule by the attachment of a lipophilic isoprenoid group. Isoprenoids are a diverse family of lipophilic molecules based on a repeating 5-carbon structure. Farnesyl diphosphate, a 15-carbon molecule, and geranylgeranyl diphosphate, a 20-carbon molecule, are the isoprenoid compounds most relevant to protein prenylation.

Many specific proteins are post-translationally modified with a prenyl group. Most, if not all, prenylated proteins are modified by the attachment of either a 15-carbon farnesyl or a 20-carbon geranylgeranyl group (Rilling, H. C. et al., Science, 247:318–320 (1990)) in a thioether linkage to a cysteine residue. In most organisms geranylgeranylation is a more common modification than farnesylation, although the relative proportions of farnesyl cysteine and geranylgeranyl cysteine in total cellular protein varies somewhat between organisms and cell types (Epstein, W. W. et al., PNAS, USA, 88:9668–7019 (1991)). Prenylated proteins are found in a variety of cellular compartments, including the nucleus, the cytosol, and membrane-bound organelles (Maltese, W. A. and Sheridan, K. M., J. Cell. Physiol., 133:471–81 (1987)).

Most of the prenylated proteins whose identities have been determined belong to one of four protein families: small GTP-binding proteins, lipopeptide pheromones, nuclear lamins, and trimeric G-proteins. Most of the known prenylated proteins are members of the Ras superfamily of low-molecular-weight guanine nucleotide-binding proteins. These proteins can be divided into four smaller protein families: the Ras, Rho, Rap and Rab/Ypt families (Chardin, P., Biochimie, 70:865–68 (1988)). These proteins participate in a variety of cellular functions, including control of cell growth and differentiation, cytokinesis, and membrane trafficking. All small GTP-binding proteins contain cysteine residues at or near the carboxyl-terminus that appear to serve as targets for post-translational prenylation.

The Ras proteins are plasma membrane-localized molecules that regulate cell differentiation and proliferation in mammalian and yeast cells. Ras proteins contain a carboxyl-terminal sequence called a CaaX motif with a cysteine followed by 2 aliphatic residues and a carboxyl-terminal X residue which can be C, S, M, Q, or A (Taparowsky, E. et al., Cell, 34:581–86 (1983)). Genetic or pharmacological inhibition of protein prenylation blocks the membrane association and biological activity of both human and yeast Ras proteins (Hancock, J. F. et al., Cell, 57:1167–77 (1989) and Schafer, W. R. et al., Science, 245:379–85 (1989)).

A second group of small GTP-binding proteins contains a carboxyl-terminal motif similar to a CaaX box, called a CaaL motif, with a leucine residue in the carboxyl-terminal position. This group includes many proteins implicated in cytokinesis such as the Rap and Rho protein families. Many of these proteins are known to be geranylgeranylated, including G25K, RhoA (Katayama, M. et al., J. Biol. Chem., 266:12639–45 (1991)), Ral, Rac (Kinsella, B. T. et al., J. Biol. Chem., 266:9786–94 (1991)), and Rap 1A and 1B (Buss, J. E. et al., Mol. Cell. Biol., 11:1523–30 (1991) and Kowata, M. et al., PNAS. USA, 87:8960–64 (1990)). A prenylated carboxyl-terminus is required for the association of Rap 1B with membranes. Prenylation and phosphorylation are both required for interaction of Rap 1B with a factor known as GDS, which stimulates GDP/GTP exchange (Hata, Y. et al., J. Biol. Chem., 266:6571–77 (1991)), since prenylated, phosphorylated peptides corresponding to Rap 1B carboxylterminus can compete with intact Rap 1B for interaction with GDS, whereas other peptides lacking either modification cannot.

The Rho proteins are also localized to the Golgi (McCaffrey, M. et al., J. Cell Biol., 115:309–19 (1991)), and also appear to require geranylgeranylation for association with membranes and with exchange factors.

A third group of small GTP-binding proteins contain the carboxyl-terminal sequences C-C, C-X-C, or C-C-X-X. These proteins include most of the Rab/YPT proteins, which are involved in regulating intracellular trafficking and are present both in the cytoplasm and associated with distinct membrane compartments (Balch, W. E., Trends Biochem. Sci., 15:469–72 (1990)). Geranylgeranylation of these proteins has been shown to be essential for association of these proteins with membranes.

Geranylgeranyl pyrophosphate synthetase is involved in a branch of the cholesterol/steroid pathway of metabolism and catalyzes the trans-addition of three molecules of isopentenyl diphosphate onto dimethylallyl diphosphate to form the $C^{20}$ geranylgeranyl pyrophosphate (GGPP). As stated above GGPP is used as a prenyl protein modification group to modify proteins and control signal transduction and activation of these proteins and trafficking of these proteins.

The polypeptide of the present invention has been putatively identified as a human geranylgeranyl pyrophosphate synthetase. This identification has been made as a result of amino acid sequence homology.

In accordance with one aspect of the present invention, there is provided a novel mature polypeptide which is hGGPS, as well as biologically active and diagnostically or therapeutically useful fragments, analogs and derivatives thereof.

In accordance with another aspect of the present invention, there are provided isolated nucleic acid molecules encoding hGGPS, including mRNAs, DNAs, cDNAs, genomic DNA as well as biologically active and diagnostically or therapeutically useful fragments, analogs and derivatives thereof.

In accordance with yet a further aspect of the present invention, there is provided a process for producing such polypeptide by recombinant techniques which comprises culturing recombinant prokaryotic and/or eukaryotic host cells, containing a hGGPS nucleic acid sequence, under conditions promoting expression of said protein and subsequent recovery of said protein.

In accordance with yet a further aspect of the present invention, there is provided a process for utilizing such polypeptide, or polynucleotide encoding such polypeptide, for therapeutic purposes, for example, to control the morphology of cells, to suppress apoptosis and to screen for antagonists and/or agonists.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, in the treatment of neoplasia, for example tumors and cancer cell growth, and to prevent viral proliferation.

In accordance with another aspect of the present invention there are provided nucleic acid probes comprising nucleic acid molecules of sufficient length to specifically hybridize to hGGPS sequences.

In accordance with another aspect of the present invention there is provided a method of diagnosing a disease or a susceptibility to a disease related to a mutation in hGGPS nucleic acid sequences and the protein encoded by such nucleic acid sequences.

In accordance with still another aspect of the present invention, there are provided processes for employing the disclosed polynucleotides and polypeptides for research purposes.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 shows the CDNA and (SEQ ID NO:1) corresponding deduced amino acid sequence (SEQ ID NO:2) of the hGGPS polypeptide. The polypeptide shown is the full protein sequence of the polypeptide. The standard one letter abbreviations for amino acids are used. Sequencing was performed using a 373 Automated DNA sequencer (Applied Biosystems, Inc.). Sequencing accuracy is predicted to be greater than 97% accurate.

FIG. 2 illustrates the amino acid sequence homology between the hGGPS polypeptide and geranylgeranyl pyrophosphate synthetase from Neurospora crassa.

FIG. 3 depicts an amino acid sequence homology between GGPS from Neurospora crassa, and hGGPS of the present invention. Where amino acids are identical the abbreviation for the amino acid is shown on a line below labeled consensus.

In accordance with an aspect of the present invention, there is provided an isolated nucleic acid (polynucleotide) which encodes for the mature polypeptide having the deduced amino acid sequence of FIG. 1 (SEQ ID No. 2) or for the mature polypeptide encoded by the cDNA of the clone deposited as ATCC Deposit No. 75900 on Sep. 28, 1994.

The ATCC number referred to above is directed to a biological deposit with the ATCC, 12301 Parklawn Drive, Rockville, Md. 20852. The strain is being maintained under the terms of the Budapest Treaty and will be made available to a patent office signatory to the Budapest Treaty.

The polynucleotide of this invention was discovered in cDNA library derived from human fetal heart. It is structurally related to the polyprenyl synthetase family. It contains an open reading frame encoding a protein of 300 amino acid residues. The protein exhibits the highest degree of homology to GGPS from Neurospora crassa with 54% identity and 72% similarity over a 265 amino acid stretch. hGGPS contains both conserved aspartate motifs that denote this family of proteins, namely LLIDDEIDNSKLRRG and LGLFFQIRDDYAN (see FIG. 1). The putative active site domain of the polypeptide of the present invention is from amino acid 147 to amino 154 of SEQ ID NO:2.

The polynucleotide of the present invention may be in the form of RNA or in the form of DNA, which DNA includes CDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID No. 1) or that of the deposited clone or may be a different coding sequence which coding sequence, as a result of the redundancy or degeneracy of the genetic code, encodes the same mature polypeptide as the DNA of FIG. 1 (SEQ ID No. 1) or the deposited cDNA.

The polynucleotide which encodes for the mature polypeptide of FIG. 1 (SEQ ID No. 2) or for the mature polypeptide encoded by the deposited cDNA may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID No. 2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID No. 2) or the same mature polypeptide encoded by the cDNA of the deposited clone as well as variants of such polynucleotides which variants encode for a fragment, derivative or analog of the polypeptide of FIG. 1 (SEQ ID No. 2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID No. 1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, L, et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length CDNA and to isolate other cDNAs which have a high sequence similarity to the gene or similar biological activity. Probes of this type preferably, have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to an hGGPS polypeptide which has the deduced amino acid sequence of FIG. 1 (SEQ ID No. 2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID No. 2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID No. 2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol). Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the hGGPS genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli,* Streptomyces, *Salmonella typhimurium;* fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, PMSG, pSVL (Pharmacia). However, any other plasmid or vector may be used as long as they are replicable and viable in the host.

Promoter regions can be selected from any desired gene using CAT e(chloramphenicol transferase) vectors or other vectors with selectable markers. Two appropriate vectors are PKK232-8 and PCM7. Particular named bacterial promoters include laci, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-L Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The hGGPS polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The hGGPS polypeptide may be employed in a method of screening compounds to identify those which block (antagonists) the activity of hGGPS and the resultant formation of GGPP. There are numerous methods for this type of screening, for example, subtle specificity may reside in the recognition of different protein substrates, which may be employed in assays which assess binding of GGPS to these proteins or peptide substrates or in enzymatic readouts. Also, an assay may be configured using a substrate analog.

As an example, antagonist activity may be determined by measuring the amount of GGPP synthesized from a molar excess of isopentenyl diphosphate, dimethylallyl diphosphate in the presence of hGGPS and a compound to be screened. The reaction is carried out in the presence of a reaction mixture and under reaction conditions which facilitate the formation of GGPP. The substrates listed above are for illustration only and numerous substrates may be employed in the assay. The ability of the compound to be screened to antagonize the properties of hGGPS are determined by measuring the amount of GGPP synthesized and comparing that amount to the amount of GGPP synthesized in the absence of the compound. GGPP may be purified by HPLC and a Lowry assay may be used to measure the amount of protein. The GGPP may also be identified by amino acid sequence analysis.

Human GGPS is produced and functions intra-cellularly, therefore, any antagonists must be intra-cellular. Potential antagonists to hGGPS include antibodies which are produced intra-cellularly. For example, an antibody identified as antagonizing hGGPS may be produced intra-cellularly as a single chain antibody by procedures known in the art, such as transforming the appropriate cells with DNA encoding the single chain antibody to prevent the function of hGGPS.

Another potential hGGPS antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al, Science, 241:456 (1988); and Dervan et al., Science, 251: 1360 (1991)), thereby preventing transcription and the production of hGGPS. The antisense RNA oligonucleotide hybridizes to the mRNA in vivo and blocks translation of the mRNA molecule into the hGGPS polypeptide (Antisense - Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of hGGPS.

Potential hGGPS antagonists also include small molecules, which are able to pass through the cell membrane, and bind to and occupy the catalytic site of the polypeptide thereby making the catalytic site inaccessible to substrate such that normal biological activity is prevented. Examples of small molecules include but are not limited to small peptides or peptide-like molecules.

The hGGPS polypeptides and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Mpyeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human Cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Once the hGGPS polypeptide is being expressed intracellularly via gene therapy, it may be employed to modify central signal transduction protein and, therefore, treat many diseases. For example, hGGPS may be employed to increase the presence of GGPP and restore the proper morphologic phenotype to cells, since in the absence of protein prenylation, cells develop a round, retractile morphology. This is due to the selective loss of actin cables without gross changes in the microtubular lattice or intermediate filament structure. This indicates that prenylated proteins play a critical role in regulating the state of intracellular actin and the general morphology of cells, which is important in patients undergoing treatment with HMG-COA Reductase inhibitors, such as lovastatin, for high cholesterol conditions.

hGGPS may also be employed to treat rhabdomyolysis, which is a side effect of HMG-CoA Reductase inhibitor treatment, where muscle cell shape is controlled.

The hGGPS polypeptide may also be employed to suppress programmed cell death or apoptosis. Lovastatin, an inhibitor of mevalonate synthesis, causes cells to exhibit alterations in growth and morphology and thus the cells eventually are induced to die via apoptosis. Mevalonate is the precursor of isoprenoid lipids. This points to the involvement of isoprenylated proteins in the mechanisms suppressing cell death.

In accordance with yet a further aspect of the present invention, there is provided a process for utilizing such polypeptides, or polynucleotides encoding such polypeptides, as a research reagent for in vitro purposes related to scientific research, synthesis of DNA and manufacture of DNA vectors, for the purpose of developing therapeutics and diagnostics for the treatment of human disease.

The hGGPS antagonists may be employed to prevent neoplastic transformation of cells which lead to cancer. Certain proteins which do not have the prenyl group from the prenyl pyrophosphate transferred to the cysteine residue of the Caa box of these proteins cannot effect interaction with the membrane so that neoplastic transformation of cells is prevented. In short, certain proto-oncogene products must have prenylation to express their oncogenic potential.

The hGGPS antagonists may be employed to treat prevent viral envelope precursors from reaching the Golgi compartment by blocking the isoprenylation of rab proteins required for endoplasmic reticulum to Golgi transport.

The antagonists, in the case of antagonists capable of passing through a cell membrane, may be employed in a composition with a pharmaceutically acceptable carrier, e.g., as hereinafter described.

This invention is also related to the use of the hGGPS gene as part of a diagnostic assay for detecting diseases or susceptibility to diseases related to the presence of mutated hGGPS nucleic acid sequences. Such diseases are related to abnormal cell morphology, cell death and human choroideremia, an X-linked form of retinal degeneration is caused by a mutation in the geranylgeranyl transferase gene.

Individuals carrying mutations in the hGGPS gene may be detected at the DNA level by a variety of techniques. Nucleic acids for diagnosis may be obtained from a patient's cells, such as from blood, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding hGGPS can be used to identify and analyze hGGPS mutations. For example, deletions and insertions can be detected by a change in size of the amplified product in comparison to the normal genotype. Point mutations can be identified by hybridizing amplified DNA to radiolabeled hGGPS RNA or alternatively, radiolabeled hGGPS antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of hGGPS protein in various tissues since an over-expression of the proteins compared to normal control tissue samples is indicative of an increase in membrane localization of oncogenic/signal transduction proteins which in turn may mark increased growth of cells involved in cancer. Assays used to detect levels of hGGPS protein in a sample derived from a host are well-known to those of skill in the art and include radioimmunoassays, competitive-binding assays, Western Blot analysis, ELISA assays and "sandwich" assay.

An ELISA assay (Coligan, et al., Current Protocols in Immunology, 1(2), Chapter 6, (1991)) initially comprises preparing an antibody specific to the hGGPS antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any hGGPS proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to hGGPS. Unattached reporter antibody is then washed out. Peroxidase substrates are then added to the dish and the amount of color developed in a given time period is a measurement of the amount of hGGPS protein present in a given volume of patient sample when compared against a standard curve.

A competition assay may be employed wherein antibodies specific to hGGPS are attached to a solid support and labeled hGGPS and a sample derived from the host are passed over the solid support and the amount of label detected, for example by liquid scintillation chromatography, can be correlated to a quantity of hGGPS in the sample.

A "sandwich" assay is similar to an ELISA assay. In a "sandwich" assay hGGPS is passed over a solid support and binds to antibody attached to a solid support. A second antibody is then bound to the hGGPS. A third antibody which is labeled and specific to the second antibody is then passed over the solid support and binds to the second antibody and an amount can then be quantified.

The hGGPS polypeptides and antagonists, may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The sequences of the present invention are also valuable for chromosome identification. The sequence is specifically targeted to and can hybridize with a particular location on an individual human chromosome. Moreover, there is a current seed for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. computer analysis of the 3' untranslated regions is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res.. 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1
Bacterial Expression and Purification of hGGPS

The DNA sequence encoding hGGPS, ATCC # 75900, is initially amplified using PCR oligonucleotide primers corresponding to the 5' and 3' end sequences of the processed hGGPS nucleic acid sequence. Additional nucleotides corresponding to hGGPS are added to the 5' and 3' sequences respectively. The 5' oligonucleotide primer has the sequence 5' AGAGGATCCGCCATGGAGAAGACTCAAGAA 3' (SEQ ID No. 3) contains a Bam HI restriction enzyme site (underlined) followed by 18 nucleotides of hGGPS coding sequence starting from the presumed terminal amino acid of the processed protein. The 3' sequence 5' CGTTGGCTAGCCTTATTCATTTTCTTCTTTGGA 3' (SEQ ID No. 4) contains complementary sequences to NheI site and is followed by 18 nucleotides of hGGPS. The restriction enzyme sites correspond to the restriction enzyme sites on the bacterial expression vector pQE-9 (Qiagen, Inc. Chatsworth, Calif.). pQE-9 encodes antibiotic resistance (Ampr), a bacterial origin of replication (ori), an IPTG-regulatable promoter operator (P/O), a ribosome binding site (RBS), a 6-His tag and restriction enzyme sites. pQE-9 is then digested with Bam HI and XbaI. The amplified sequences are ligated into pQE-9 and are inserted in frame with the sequence encoding for the histidine tag and the RBS. The ligation mixture is then used to transform *E. coli* M15 strain available from Qiagen under the trademark M15/rep 4 by the procedure described in Sambrook. J. et al., Molecular Cloning: A Laboratory Manual, Cold Spring Laboratory Press, (1989) M15/rep4 contains multiple copies of the plasmid pREP4, which expresses the laci repressor and also confers kanamycin resistance (Kanr). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the laci repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized hGGPS is purified from this solution by chromatography on a Nickel-Chelate column under conditions that allow for tight binding by proteins containing the 6-His tag (Hochuli, E. et al., J. Chromatography 411:177–184 (1984)). hGGPS (90% pure) is eluted from the column in 6 molar guanidine HCl pH 5.0 and for the purpose of renaturation adjusted to 3 molar guanidine HCl, 100 mM sodium phosphate, 10 mmolar glutathione (reduced) and 2 molar glutathione (oxidized). After incubation in this solution for 12 hours the protein is dialyzed to 10 mmolar sodium phosphate.

EXAMPLE 2
Cloning and expression of hGGPS using the baculovirus expression system The DNA sequence encoding the full length hGGPS protein, ATCC # 75900, is amplified using PCR oligonucleotide primers corresponding to the 5' and 3' sequences of the gene:

The 5' primer has the sequence 5' GCCAGAGGATCCGCCACCATG GAGAAGACTCAAGAAACA 3' (SEQ ID No. 5) and contains a BamHI restriction enzyme site (in bold) followed by 6 nucleotides resembling an efficient signal for the initiation of translation in eukaryotic cells (Kozak, M., J. Mol. Biol., 196:947–950 (1987) which is just behind the first 21 nucleotides of the hGGPS gene (the initiation codon for translation "ATG" is underlined).

The 3' primer has the sequence 5' CGTTGGCTAGCCTTATTCAT TTTCTTCTTTGGA 3' (SEQ ID No. 6) and contains the cleavage site for the restriction endonuclease NheI and 18 nucleotides complementary to the 3' non-translated sequence of the hGGPS gene. The amplified sequences are isolated from a 1% agarose gel using a commercially available kit ("Geneclean," BIO 101 Inc., La Jolla, Calif.). The fragment is then digested with the endonucleases BamHI and NheI and then purified again on a 1% agarose gel. This fragment is designated F2.

The vector pA2 (modification of pVL941 vector, discussed below) is used for the expression of the hGGPS protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica nuclear polyhedrosis* virus (AcMNPV) followed by the recognition sites for the restriction endonucleases BamHI and XbaI. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes BamHI and XbaI. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E. coli* HB101 cells are then transformed and bacteria identified that contained the plasmid (pBac hGGPS) with the hGGPS gene using the enzymes BAmHI and PstI. The sequence of the cloned fragment is confirmed by DNA sequencing.

5 μg of the plasmid pBac-hGGPS is co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBachGGPS are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace' medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-hGGPS at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labelled proteins visualized by SDS-PAGE and autoradiography.

EXAMPLE 3
Expression of Recombinant hGGPS in COS cells

The expression of plasmid, hGGPS HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire hGGPS precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding hGGPS, ATCC # 75900, is constructed by PCR using two primers: the 5' primer 5' GCCAGAGGATCCATGGAGAAGACTCAAGAAACA 3' (SEQ ID No. 7) contains a BamHI site followed by 21 nucleotides of hGGPS coding sequence starting from the initiation codon; the 3' sequence 5' CGGCTGCTAGCCT-CAAGCGTAGTCTGGGACGTCGTATGGGTATTCATT TTCTTCTTTGGA 3' (SEQ ID No. 8) contains complementary sequences to an NheI site, translation stop codon, HA tag and the last 18 nucleotides of the hGGPS coding sequence (not including the stop codon). Therefore, the PCR product contains a BamHI site, hGGPS coding sequence followed by HA tag fused in frame, a translation termination stop codon next to the HA tag, and an NheI site. The PCR amplified DNA fragment and the vector, pcDNAI/Amp, are digested with BamHI and NheI restriction enzyme and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant hGGPS, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the hGGPS-HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 4
Expression pattern of hGGPS in human tissue

Northern blot analysis is carried out to examine the levels of expression of hGGPS in human tissues. Total cellular RNA samples are isolated with RNAzol™ system (Biotecx Laboratories, Inc. Houston, Tex.). About 10 μg of total RNA isolated from each human tissue specified is separated on 1% agarose gel and blotted onto a nylon filter. (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column. (5 Prime - 3 Prime, Inc. Boulder, Colo.). The filter is then hybridized with radioactive labeled full length hGGPS gene at 1,000,000 cpm/ml in 0.5M NaPO$_4$, pH 7.4 and 7% SDS overnight at 65° C. After wash twice at room temperature and twice at 60° C. with 0.5×SSC, 0.1% SDS, the filter is then exposed at −70° C. overnight with an intensifying screen.

EXAMPLE 5
Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The CDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least 95% identity to a member selected from the group consisting of:
  (a) a polynucleotide encoding a polypeptide comprising the amino acid sequence from amino acid 2 to 300 of SEQ ID NO:2; and
  (b) the complement of (a).

2. The isolated polynucleotide of claim 1 wherein said member is (a).

3. The isolated polynucleotide of claim 1 wherein said member is (a) and the polypeptide comprises amino acids 1 to 300 of SEQ ID No:2.

4. The isolated polynucleotide of claim 1 comprising a polynucleotide encoding a polypeptide comprising the amino acid sequence identical to amino acids 2 to 300 of SEQ ID NO:2.

5. The isolated polynucleotide of claim 4 comprising nucleotides 4 to 903 of SEQ ID NO:1.

6. The isolated polynucleotide of claim 4 comprising nucleotides 1 to 903 of SEQ ID NO:1.

7. The isolated polynucleotide of claim 2, wherein the polynucleotide is DNA.

8. The isolated polynucleotide of claim 1 comprising a polynucleotide encoding a polypeptide comprising the amino sequence identical to amino acids 1 to 300 of SEQ ID NO:2.

9. The isolated polynucleotide of claim 1 wherein said polynucleotide is RNA.

10. An isolated polynucleotide comprising a polynucleotide having at least a 95% identity to a member selected from the group consisting of:
  (a) a polynucleotide encoding the same mature polypeptide encoded by the human cDNA in ATCC Deposit No. 75900; and
  (b) the complement of (a).

11. The isolated polynucleotide of claim 10, wherein the member is (a).

12. The isolated polynucleotide of claim 10, wherein said polynucleotide comprises DNA identical to the coding portion of the human cDNA in ATCC Deposit No. 75900 which encodes a mature polypeptide.

13. A method of making a recombinant vector comprising inserting the isolated polynucleotide of claim 2 into a vector, wherein said polynucleotide is DNA.

14. A recombinant vector comprising the polynucleotide of claim 2, wherein said polynucleotide is DNA.

15. A recombinant host cell comprising the polynucleotide of claim 2, wherein said polynucleotide is DNA.

16. A method for producing a polypeptide comprising expressing from the recombinant cell of claim 15 the polypeptide encoded by said polynucleotide.

17. A process for producing a polypeptide comprising:
  expressing from a recombinant cell containing the polynucleotide of claim 4 the polypeptide encoded by said polynucleotide.

18. A process for producing a polypeptide comprising:
  expressing from a recombinant cell containing the polynucleotide of claim 8 the polypeptide encoded by said polynucleotide.

* * * * *

UNITED STATES PATENT AND TRADEMARK OFFICE
CERTIFICATE OF CORRECTION

PATENT : 5,786,193
DATED : July 28, 1998
INVENTOR(S) : John M. Greene, Ewen F. Kirkness, and Craig A. Rosen

It is certified that error appears in the above-identified patent and that said Letters Patent is hereby corrected as shown below:

On the title page, insert the following:
--[63] Continuation-in-part of application No. PCT/US95/00421, Jan. 11, 1995.--

In column 1, line 3, after the title, insert the following:
--This application is a continuation-in-part of and claims priority under 35 U.S.C. §120 TO PCT/US95/00421, filed Jan. 11, 1995.--.

Signed and Sealed this

Thirtieth Day of May, 2000

Attest:

Q. TODD DICKINSON

*Attesting Officer*   *Director of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 903 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:1:

```
ATGGAGAAGA  CTCAAGAAAC  AGTCCAAAGA  ATTCTTCTAG  AACCCTATAA  ATACTTACTT    60

CAGTTACCAG  GTAAACAAGT  GAGAACCAAA  CTTTCACAGG  CATTTAATCA  TTGGCTGAAA   120

GTTCCAGAGG  ACAAGCTACA  GATTATTATT  GAAGTGACAG  AAATGTTGCA  TAATGCCAGT   180

TTACTCATCG  ATGATATTGA  AGACAACTCA  AAACTCCGAC  GTGGCTTTCC  AGTGGCCCAC   240

AGCATCTATG  GAATCCCATC  TGTCATCAAT  TCTGCCAATT  ACGTGTATTT  CCTTGGCTTG   300

GAGAAAGTCT  TAACCCTTGA  TCACCCAGAT  GCAGTGAAGC  TTTTTACCCG  CCAGCTTTTG   360

GAACTCCATC  AGGGACAAGG  CCTAGATATT  TACTGGAGGG  ATAATTACAC  TTGTCCCACT   420

GAAGAAGAAT  ATAAAGCTAT  GGTGCTGCAG  AAAACAGGTG  GACTGTTTGG  ATTAGCAGTA   480

GGTCTCATGC  AGTTGTTCTC  TGATTACAAA  GAAGATTTAA  AACCGCTACT  TAATACACTT   540

GGGCTCTTTT  TCCAAATTAG  GGATGATTAT  GCTAATCTAC  ACTCCAAAGA  ATATAGTGAA   600
```

```
AACAAAAGTT  TGGGTGAAGA  TCTGACAGAG  GGAAAGTTCT  CATTTCCTAC  TATTCATGCT    660

ATTTGGTCAA  GGTCTGAAAG  CACCCAGGTG  CAGAATATCT  TGCGCCAGAG  AACAGAAAAC    720

ATAGATATAA  AAAAATACTG  TGTACATTAT  CTTGAGGATG  TAGGTTCTGG  GGAATACACT    780

CGTAATACCC  TTAAAGAGCT  TGAAGCTAAA  GCCTATAAAC  AGATTGATGC  ACGTGGTGGG    840

AACCCTGAGC  TAGTAGCCTT  AGTAAAACAC  TTAAGTAAGA  TGTCCAAAGA  AGAAAATGAA    900

TAA                                                                      903
```

( 2 ) INFORMATION FOR SEQ ID NO:2:

( i ) SEQUENCE CHARACTERISTICS:
        ( A ) LENGTH: 300 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

```
Met  Glu  Lys  Thr  Gln  Glu  Thr  Val  Gln  Arg  Ile  Leu  Leu  Glu  Pro
                    5                   10                            15

Tyr  Lys  Tyr  Leu  Leu  Gln  Leu  Pro  Gly  Lys  Gln  Val  Arg  Thr  Lys
                    20                  25                            30

Leu  Ser  Gln  Ala  Phe  Asn  His  Trp  Leu  Lys  Val  Pro  Glu  Asp  Lys
                    35                  40                            45

Leu  Gln  Ile  Ile  Ile  Glu  Val  Thr  Glu  Met  Leu  His  Asn  Ala  Ser
                    50                  55                            60

Leu  Leu  Ile  Asp  Asp  Ile  Glu  Asp  Asn  Ser  Lys  Leu  Arg  Arg  Gly
                    65                  70                            75

Phe  Pro  Val  Ala  His  Ser  Ile  Tyr  Gly  Ile  Pro  Ser  Val  Ile  Asn
                    80                  85                            90

Ser  Ala  Asn  Tyr  Val  Tyr  Phe  Leu  Gly  Leu  Glu  Lys  Val  Leu  Thr
                    95                  100                           105

Leu  Asp  His  Pro  Asp  Ala  Val  Lys  Leu  Phe  Thr  Arg  Gln  Leu  Leu
                    110                 115                           120

Glu  Leu  His  Gln  Gly  Gln  Gly  Leu  Asp  Ile  Tyr  Trp  Arg  Asp  Asn
                    125                 130                           135

Tyr  Thr  Cys  Pro  Thr  Glu  Glu  Glu  Tyr  Lys  Ala  Met  Val  Leu  Gln
                    140                 145                           150

Lys  Thr  Gly  Gly  Leu  Phe  Gly  Leu  Ala  Val  Gly  Leu  Met  Gln  Leu
                    155                 160                           165

Phe  Ser  Asp  Tyr  Lys  Glu  Asp  Leu  Lys  Pro  Leu  Leu  Asn  Thr  Leu
                    170                 175                           180

Gly  Leu  Phe  Phe  Gln  Ile  Arg  Asp  Asp  Tyr  Ala  Asn  Leu  His  Ser
                    185                 190                           195

Lys  Glu  Tyr  Ser  Glu  Asn  Lys  Ser  Leu  Gly  Glu  Asp  Leu  Thr  Glu
                    200                 205                           210

Gly  Lys  Phe  Ser  Phe  Pro  Thr  Ile  His  Ala  Ile  Trp  Ser  Arg  Ser
                    215                 220                           225

Glu  Ser  Thr  Gln  Val  Gln  Asn  Ile  Leu  Arg  Gln  Arg  Thr  Glu  Asn
                    230                 235                           240

Ile  Asp  Ile  Lys  Lys  Tyr  Cys  Val  His  Tyr  Leu  Glu  Asp  Val  Gly
                    245                 250                           255

Ser  Gly  Glu  Tyr  Thr  Arg  Asn  Thr  Leu  Lys  Glu  Leu  Glu  Ala  Lys
                    260                 265                           270

Ala  Tyr  Lys  Gln  Ile  Asp  Ala  Arg  Gly  Gly  Asn  Pro  Glu  Leu  Val
```

|   | 275 |   |   |   |   | 280 |   |   |   |   | 285 |   |
|---|---|---|---|---|---|---|---|---|---|---|---|---|
| Ala | Leu | Val | Lys | His | Leu | Ser | Lys | Met | Ser | Lys | Glu | Glu | Asn | Glu |
|   |   |   |   | 290 |   |   |   |   | 295 |   |   |   |   | 300 |

( 2 ) INFORMATION FOR SEQ ID NO:3:

( i ) SEQUENCE CHARACTERISTICS:
        ( A ) LENGTH: 30 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:3:

AGAGGATCCG CCATGGAGAA GACTCAAGAA                              30

( 2 ) INFORMATION FOR SEQ ID NO:4:

( i ) SEQUENCE CHARACTERISTICS:
        ( A ) LENGTH: 33 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:4:

CGTTGGCTAG CCTTATTCAT TTTCTTCTTT GGA                         33

( 2 ) INFORMATION FOR SEQ ID NO:5:

( i ) SEQUENCE CHARACTERISTICS:
        ( A ) LENGTH: 39 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:5:

GCCAGAGGAT CCGCCACCAT GGAGAAGACT CAAGAAACA                 39

( 2 ) INFORMATION FOR SEQ ID NO:6:

( i ) SEQUENCE CHARACTERISTICS:
        ( A ) LENGTH: 33 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:6:

CGTTGGCTAG CCTTATTCAT TTTCTTCTTT GGA                         33

( 2 ) INFORMATION FOR SEQ ID NO:7:

( i ) SEQUENCE CHARACTERISTICS:
        ( A ) LENGTH: 33 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:7:

GCCAGAGGAT CCATGGAGAA GACTCAAGAA ACA                         33

( 2 ) INFORMATION FOR SEQ ID NO:8:

( i ) SEQUENCE CHARACTERISTICS:
    ( A ) LENGTH: 60 BASE PAIRS
    ( B ) TYPE: NUCLEIC ACID
    ( C ) STRANDEDNESS: SINGLE
    ( D ) TOPOLOGY: LINEAR ( i i ) MOLECULE TYPE: Oligonucleotide ( x i ) SEQUENCE DESCRIPTION: SEQ ID NO:8:

```
CGGCTGCTAG  CCTCAAGCGT  AGTCTGGGAC  GTCGTATGGG  TATTCATTTT  CTTCTTTGGA        60
```